(12) United States Patent
Nathan et al.

(10) Patent No.: US 7,026,374 B2
(45) Date of Patent: Apr. 11, 2006

(54) INJECTABLE MICRODISPERSIONS FOR MEDICAL APPLICATIONS

(76) Inventors: Aruna Nathan, 16 Woodward Dr., Bridgewater, NJ (US) 08807; Joel Rosenblatt, 47 Robin Glen Rd., Watchung, NJ (US) 07060; Steven C. Arnold, 26 Hideaway La., Sparta, NJ (US) 07871

( * ) Notice: Subject to any disclaimer, the term of this patent is extended or adjusted under 35 U.S.C. 154(b) by 377 days.

(21) Appl. No.: 10/178,970

(22) Filed: Jun. 25, 2002

(65) Prior Publication Data

US 2003/0236310 A1    Dec. 25, 2003

(51) Int. Cl.
C08L 15/00 (2006.01)
A61F 2/00 (2006.01)

(52) U.S. Cl. .................. 523/113; 523/114; 523/115; 523/122; 524/417

(58) Field of Classification Search .............. None
See application file for complete search history.

(56) References Cited

U.S. PATENT DOCUMENTS

| | | |
|---|---|---|
| 2,895,930 A | 7/1959 | Milton |
| 3,278,464 A | 10/1966 | Boyer et al. |
| 3,806,479 A | 4/1974 | Cunningham et al. |
| 3,978,203 A | 8/1976 | Wise |
| 3,997,512 A | 12/1976 | Casey et al. |
| 3,997,627 A * | 12/1976 | Ichimura et al. ............ 526/320 |
| 4,048,256 A | 9/1977 | Casey et al. |
| 4,076,798 A | 2/1978 | Casey et al. |
| 4,095,600 A | 6/1978 | Casey et al. |
| 4,118,470 A | 10/1978 | Casey et al. |
| 4,122,129 A | 10/1978 | Casey et al. |
| 4,163,073 A | 7/1979 | Pepe et al. |
| 4,384,975 A | 5/1983 | Fong |
| 4,419,139 A | 12/1983 | Gooch et al. |
| 4,568,559 A | 2/1986 | Nuwayser et al. |
| 5,137,743 A | 8/1992 | Zaks |
| 5,155,246 A | 10/1992 | Naskar et al. |
| 5,219,980 A | 6/1993 | Swidler |
| 5,306,311 A | 4/1994 | Stone et al. |
| 5,308,623 A | 5/1994 | Fues et al. |
| 5,360,626 A | 11/1994 | Iyengar |
| 5,411,554 A | 5/1995 | Scopelianos et al. |
| 5,442,033 A | 8/1995 | Bezwada |
| 5,464,929 A | 11/1995 | Bezwada et al. |
| 5,525,646 A | 6/1996 | Lundgren et al. |
| 5,599,852 A | 2/1997 | Scopelianos et al. |
| 5,607,687 A | 3/1997 | Bezwada et al. |
| 5,618,552 A | 4/1997 | Bezwada et al. |
| 5,628,993 A | 5/1997 | Yamagata et al. |
| 5,631,015 A | 5/1997 | Bezwada et al. |
| 5,653,992 A | 8/1997 | Bezwada et al. |
| 5,670,478 A | 9/1997 | Stuchlik et al. |
| 5,698,213 A | 12/1997 | Jamiolkowski et al. |
| 5,700,583 A | 12/1997 | Jamiolkowski et al. |
| 5,728,752 A | 3/1998 | Scopelianos et al. |
| 5,750,100 A | 5/1998 | Yamagata et al. |
| 5,753,234 A | 5/1998 | Lee et al. |
| 5,824,333 A | 10/1998 | Scopelianos et al. |
| 5,859,150 A | 1/1999 | Jamiolkowski et al. |
| 5,998,552 A | 12/1999 | Gruber et al. |
| 6,074,660 A | 6/2000 | Jamiolkowski et al. |
| 6,100,346 A | 8/2000 | Jamiolkowski et al. |
| 6,110,501 A | 8/2000 | Redding, Jr. et al. |
| 6,114,458 A | 9/2000 | Hawker et al. |
| 6,120,787 A | 9/2000 | Gustafsson et al. |
| 6,121,398 A | 9/2000 | Wool et al. |
| 6,147,168 A | 11/2000 | Jamiolkowski et al. |
| 6,224,894 B1 | 5/2001 | Jamiolkowski et al. |
| 6,251,435 B1 | 6/2001 | Jamiolkowski et al. |
| 6,268,329 B1 | 7/2001 | Markussen |
| 6,335,383 B1 | 1/2002 | Scopelianos et al. |
| 2002/0037301 A1 | 3/2002 | De La Poterie |
| 2003/0185752 A1 | 10/2003 | Nathan et al. |

FOREIGN PATENT DOCUMENTS

| | | |
|---|---|---|
| DE | 1694845 A | 8/1971 |
| EP | 0422209 B1 | 3/1995 |
| EP | 841361 A1 | 5/1995 |
| EP | 747072 A | 12/1996 |
| EP | 1 270 024 A | 1/2003 |
| EP | 1348451 A | 10/2003 |
| EP | 1369136 A | 12/2003 |
| EP | 1374860 A | 1/2004 |
| GB | 630924 A | 10/1949 |

(Continued)

OTHER PUBLICATIONS

Brian Parkyn, F. Lamb and B. V. Clifton, "Polyesters vol. 2 Unsaturated Polyesters and Polyester Plasticisers," London Lliffe Books Ltd., New York American Elsevier Publishing Company, Inc., 1967, pp. 107-122.

(Continued)

*Primary Examiner*—Thurman K. Page
*Assistant Examiner*—Sharon Howard

(57) ABSTRACT

The present invention is directed to microdispersions and pharmaceutical compositions containing a synthetic, bioabsorbable, biocompatible liquid polymer that is the reaction product of a polybasic acid or derivative thereof, a polyol and a fatty acid, the liquid polymer having a melting point less than about 40° C., as determined by differential scanning calorimetry, and a synthetic, bioabsorbable, biocompatible polymeric wax comprising the reaction product of a polybasic acid or derivative thereof, a fatty acid and a polyol, the polymeric wax having a melting point less than about 70° C., as determined by differential scanning calorimetry.

30 Claims, No Drawings

FOREIGN PATENT DOCUMENTS

| | | |
|---|---|---|
| WO | WO 88/03785 A1 | 6/1988 |
| WO | WO 89/08694 A1 | 9/1989 |
| WO | WO 90/12604 A1 | 11/1990 |
| WO | WO 92/12645 A1 | 8/1992 |
| WO | WO 93/08850 A1 | 5/1993 |
| WO | WO 94/15079 A1 | 7/1994 |
| WO | WO 94/25079 A1 | 11/1994 |
| WO | WO 95/33821 A1 | 12/1994 |
| WO | WO 97/09367 | 3/1997 |
| WO | WO 97/23606 A1 | 7/1997 |
| WO | WO 95/22318 A1 | 8/1997 |
| WO | WO 99/29303 A1 | 6/1999 |
| WO | WO 00/02950 A1 | 1/2000 |
| WO | WO 00/35511 A | 6/2000 |
| WO | WO 00/44808 A1 | 8/2000 |
| WO | WO 01/07486 A1 | 2/2001 |
| WO | WO 01/76649 A | 10/2001 |

OTHER PUBLICATIONS

Temple C. Patton, "Alkyd Resin Technoloogy—Formulating Techniques and Allied Calculations," Interscience Publishers, John Wiley and Sons, New York—London 1962, pp. 13-31.

EPO Search Report dated Apr. 22, 2004, Apr. 23, 2004, another Apr. 23, 2004, & Apr. 28, 2004.

Database WPI Week 199430 Derwent Publications Ltd., London, GB; an 1994-248859 XP002256761 & WO 9415591 A. (Hisamitsu), Jul. 12, 1994 abstract.

EPO Search Report dated Oct. 21, 2003, for EPO Appl. No. EP 03 25 3966.

Emiko Koyama, Fumio Sanda, and Takeshi Endo, "Synthesis of Poly(ester-amide)s Derived from Optically Active Amino Alcohols," Macromol. Symp., 122, 275-280 (1997).

Emiko Koyama, Fumio Sanda, and Takeshi Endo, "Polycondensations of Hydroxycarboxylic Acids Derived from Optically Active Aminoalcohols and Acid Anhydrides—Syntheses of Functional Poly(ester-amide)s," Journal of Polymer Science: Part A: Polymer Chemistry 35, 345-352 (1997).

Donald L. Elbert, Alison B. Pratt, Matthias P. Lutolf, Sven Halstenberg, Jeffrey A. Hubbell, "Protein Delivery from Materials Formed by Self-selective Conjugate Addition Reactions," Journal of Controlled Release, 76, 11-25 (2001).

Mark H.F.: "Alkyd Resins", Encyclopedia of Polmer Sience and Engineering. A to Amorphous Polymers, New York, J. Wiley & Sons, US. vol. 1, pp. 644-648 xP002035651 *the whole document*.

* cited by examiner

INJECTABLE MICRODISPERSIONS FOR MEDICAL APPLICATIONS

FIELD OF THE INVENTION

The present invention relates to bioabsorbable and biocompatible polymeric microdispersions for use in pharmaceutical and medical applications.

BACKGROUND OF THE INVENTION

Both natural and synthetic polymers, including homopolymers and copolymers, which are both biocompatible and absorbable in vivo are known for use in the manufacture of medical devices that are implanted in body tissue and absorb over time. Examples of such medical devices include suture anchor devices, sutures, staples, surgical tacks, clips, plates and screws, drug delivery devices, adhesion prevention films and foams, and tissue adhesives.

Natural polymers may include catgut, cellulose derivatives and collagen. Natural polymers typically absorb by an enzymatic degradation process in the body.

Synthetic polymers may include aliphatic polyesters, polyanhydrides and poly(orthoester)s. Synthetic absorbable polymers typically degrade by a hydrolytic mechanism. Such synthetic absorbable polymers include homopolymers, such as poly(glycolide), poly(lactide), poly($\epsilon$-caprolactone), poly(trimethylene carbonate) and poly(p-dioxanone), and copolymers, such as poly(lactide-co-glycolide), poly($\epsilon$-caprolactone-co-glycolide), and poly(glycolide-co-trimethylene carbonate). The polymers may be statistically random copolymers, segmented copolymers, block copolymers or graft copolymers.

Several injectable, bioabsorbable microdispersions suitable for use in parenteral applications as well as soft tissue repair or augmentation materials in animals have been described. These microdispersions contain lactone repeating units, including -caprolactone trimethylene carbonate, ether lactone, glycolide, lactide, p-dioxanone, and combinations thereof. These microdispersions, however, are slow to degrade, taking over six months to be absorbed by the body.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use in drug delivery and medical devices that permit solvent-free processing techniques in preparation of medical devices and compositions and that biodegrade within 6 months.

SUMMARY OF THE INVENTION

The present invention is directed to microdispersions, medical devices and pharmaceutical compositions, each comprising a synthetic, bioabsorbable, biocompatible liquid polymer comprising the reaction product of a polybasic acid or derivative thereof, a fatty acid and a polyol, the liquid polymer having a melting point less than about 40° C., as determined by differential scanning calorimetry, and a synthetic, bioabsorbable, biocompatible polymeric wax comprising the reaction product of a polybasic acid or derivative thereof, a fatty acid and a polyol, the polymeric wax having a melting point less than about 70° C., as determined by differential scanning calorimetry.

DETAILED DESCRIPTION OF THE INVENTION

Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, bioabsorbable, biocompatible microdispersions utilized in the present invention comprise a mixture of liquid polymers and polymeric waxes. The liquid polymers and polymeric waxes are the reaction product of a polybasic acid or derivative thereof, a fatty acid, and a polyol, and may be classified as alkyd polyesters. Preferably, the liquid polymers and polymeric waxes of the present invention are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible.

Preferably, the liquid polymers, classified as alkyd polyester liquids, utilized in the present invention will have a number average molecular weight between about 1,000 daltons and about 100,000 daltons, as determined by gel permeation chromatography. The liquid polymers comprise an aliphatic polyester backbone with pendant fatty acid ester groups that exhibit relatively low melting points, e.g. less than about 40° C., preferably less than about 25° C.

The polymeric waxes utilized in the present invention may be classified as alkyd polyester waxes. As used herein, a wax is a solid, low-melting substance that is plastic when warm and, due to its relatively low molecular weight, is fluid when melted. Preferably, the polymeric waxes utilized in the present invention will have a number average molecular weight between about 1,000 g/mole and about 100,000 g/mole, as determined by gel permeation chromatography. The polymeric waxes comprise an aliphatic polyester backbone with pendant fatty acid ester groups that crystallize rapidly, depending on the fatty acid chain length, and exhibit relatively low melting points, e.g. less than about 100° C., preferably less than about 70° C. More preferably, the melting point of the polymeric wax will be between about 25° C. and about 70° C. Typically, the polymeric waxes used in the present invention will be a solid at room temperature.

Fatty acids used to prepare polymeric microdispersions utilized in the present invention may be saturated or unsaturated. For the liquid polymers, they may vary in length from $C_4$ to $C_{12}$ for saturated fatty acids, and $C_4$ to $C_{30}$ for unsaturated fatty acids. For the polymeric waxes, they may vary in length from $C_{14}$ to $C_{30}$. Examples of such fatty acids include, without limitation, stearic acid, palmitic acid, myrisitic acid, caproic acid, decanoic acid, lauric acid, linoleic acid and oleic acid.

Polyols that can be used to prepare the polymeric microdispersions include, without limitation, glycols, polyglycerols, polyglycerol esters, glycerol, sugars and sugar alcohols. Glycerol is a preferred polyhydric alcohol due to its abundance and cost.

Monoglycerides which may be used to prepare polymeric microdispersions utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides for the liquid polymers include monocaproyl glycerol, monodecanoyl glycerol, monolauroyl glycerol, monolinoleoyl glycerol, and monooleoyl glycerol. Preferred monoglycerides for the polymeric waxes include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

In certain embodiments of the invention, the polymeric microdispersion may be prepared from the polybasic acid or derivative thereof, the monoglyceride and, additionally, at least on additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

In preparing the polymeric microdispersions utilized in the present invention, the particular chemical and physical properties required of the polymeric microdispersion for a particular use must be considered. For example, changing the chemical composition can vary the physical properties, including absorption times. Copolymers can be prepared by using mixtures of diols, triol, polyols, diacids, triacids, and different monoalkanoyl glycerides to match a desired set of properties. Similarly, blends of two or more alkyd polyesters may be prepared to tailor properties for different applications.

Alkyd polyester microdispersions of the present invention can be made more hydrophobic by increasing the length of the fatty acid side chain or the length of the diacid in the backbone, or by incorporating a long chain diol. Alternatively, alkyd polyester microdispersions of the present invention can be made more hydrophilic or amphiphilic by employing hydroxy acids, such as malic, tartaric and citric acids, or some oxadiacids, in the composition, or by employing poly(ethylene glycol)s or copolymers of polyethylene glycol and polypropylene glycol, commonly known as Pluronics, in the formation of segmented block copolymers.

Copolymers containing other linkages in addition to an ester linkage also may be synthesized; for example, ester-amides, ester-carbonates, ester-anhydrides and ester urethanes, to name a few.

Polymeric microdispersions can also be prepared using functionalized liquid polymers or polymeric waxes. The functionalized liquid polymer or polymeric wax can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized. A variety of biologically active substances, hereinafter referred to as bioactive agents, can be covalently attached to these functionalized liquid polymers or polymeric waxes by known coupling chemistry to give sustained release of the bioactive agent. As used herein, bioactive agent is meant to include those substances or materials that have a therapeutic effect on mammals, e.g. pharmaceutical compounds.

In another embodiment, the polymers of the present invention may be endcapped in a variety of ways to obtain the desired properties. Endcapping reactions convert the terminal and pendant hydroxyl groups and terminal carboxyl groups into other types of chemical moieties. Typical endcapping reactions include but are not limited to alkylation and acylation reactions using common reagents such as alkyl, alkenyl, or alkynyl halides and sulfonates, acid chlorides, anhydrides, mixed anhydrides, alkyl and aryl isocyanantes and alkyl and aryl isothiocyantes. Endcapping reactions can impart new functionality to the polymers of this invention. One skilled in the art, once having the benefit of the disclosure herein, will be able to ascertain particular properties of the polymeric microdispersions required for particular purposes, and readily prepare polymeric microdispersions that provide such properties.

One skilled in the art, once having the benefit of the disclosure herein, will be able to ascertain particular properties of the liquid polymers required for particular purposes, and readily prepare polymeric microdispersions that provide such properties.

The polymerization of the alkyd polyester waxes and liquids preferably is performed under melt polycondensation conditions in the presence of an organometallic catalyst at elevated temperatures. The organometallic catalyst preferably is a tin-based catalyst e.g. stannous octoate. The catalyst preferably will be present in the mixture at a molar ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of alkyd polyester waxes and liquids can be prepared by forming an alkyd polyester prepolymer polymerized under melt polycondensation conditions, then adding at least one lactone monomer or lactone prepolymer. The mixture then would be subjected to the desired conditions of temperature and time to copolymerize the prepolymer with the lactone monomers.

The molecular weight of the prepolymer, as well as its composition, can be varied depending on the desired characteristic that the prepolymer is to impart to the copolymer. Those skilled in the art will recognize that the alkyd polyester prepolymers described herein can also be made from mixtures of more than one diol or dioxycarboxylic acid.

One of the beneficial properties of the alkyd polyester microdispersions of this invention is that the ester linkages are hydrolytically unstable, and therefore the polymer is bioabsorbable because it readily breaks down into small segments when exposed to moist body tissue. In this regard, while it is envisioned that co-reactants could be incorporated into the reaction mixture of the polybasic acid and the diol for the formation of the alkyd polyester, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

The microdispersions may contain varying amounts of the liquid carrier and the particulate material depending on the specific properties that the microdispersion is desired to have. Generally, the weight percent of fluid carrier in the microdispersion should be in the range of from about 20 to about 99 weight percent with the remainder substantially being the particulate material. Preferably, the weight percent of fluid carrier in the microdispersion should be in the range of from about 30 to about 90 weight percent with the remainder substantially being the particulate material. Most preferably the weight percent of fluid carrier in the microdispersion should be in the range of from about 50 to about 80 percent with the remainder substantially being particulate material. One skilled in the art will appreciate that, in addition to the fluid carrier and particulate material, the microdispersions may comprise other ingredients commonly utilized to prepare dispersions, e.g. surfactants, dispersants, etc.

The viscosity of the microdispersion may also vary depending on the relative amounts of the fluid carrier and the particulate material in the microdispersion as well as on the composition of the liquid polymeric carrier and the particulate material. Generally, the shear viscosity of the microdispersion will be less than 10,000 poise and preferably will be in the range of from about 20 poise to about 2,000 poise as determined by capillary rheometry.

The microdispersions can be formed by physically blending the fluid carrier with the finely ground powder of the particulate material or by grinding a suspension of large pieces of the particulate material using the fluid carrier as a lubricant until the desired particle size distribution is obtained. Generally, the particulate material will have an average particle diameter of less than about 500 microns and preferably less than 50 microns. However, it is currently preferred to mix the particulate material and the liquid carrier and raise the temperature of the blend to a temperature sufficient to melt the particulate material (melt blending). Melt blending is preferred because it simplifies the mixing operation involved in producing the microdispersion. However, it is desirable to avoid excessive heating during melt blending to avoid transesterification of the polymers.

In one embodiment of the invention, the alkyd polyester microdispersions of the present invention can be used as a pharmaceutical carrier in a drug delivery matrix, or as a cell-based carrier in a tissue engineering application. To form the matrix, the polyester wax, liquid polymer, or microdispersion would be mixed with an effective amount of a bioactive agent to form the matrix. The variety of bioactive agents that can be used in conjunction with the liquid polymer of the invention is vast. In general, bioactive agents which may be administered via pharmaceutical compositions of the invention include, without limitation, antinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics.

Rapamycin, risperidone, and erythropoietin are several bioactive agents that may be used in drug delivery matrices of the present invention.

In two particularly preferred embodiments the bioactive agents for administration in conjunction with the bioerodible polymers of the invention are antibacterial agents for the treatment of deep wounds, and antibiotics for periodontal treatment (e.g., tetracycline or the like). Other preferred drugs for use with the presently disclosed polymers include proteinaceous drugs such as growth factors or growth hormones.

The drug delivery matrix may be administered in any suitable dosage form such as oral, parenteral, buccal, occular, topical, vaginal routes or as a suppository. Bioerodible ointments, gels, creams, and similar soft dosage forms adapted for administration via the above routes may also be formulated. Other modes of administration (e.g., transdermal) and compositional forms (e.g., more rigid transdermal forms) are within the scope of the invention as well.

Parenteral administration of a bioerodible composition of the invention can be effected by either subcutaneous, or intramuscular injection. Parenteral formulations of the polymeric microdispersion may be formulated by mixing one or more pharmaceuticals with the polymeric microdispersion. Other suitable parenteral additives may be formulated with the microdispersion and pharmaceutical active. However, if water is to be used it should be added immediately before administration or the water containing microdispersion should be stored at a temperature sufficiently low so as to minimize hydrolysis of the polymeric microdispersion. Bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible microdispersions of the invention will include an ointment, gel or cream base comprising one or more of the copolymers described herein and a selected bioactive agent. The bioactive agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide, ethanol, eucalyptol, lecithin, and the 1-N-dodecylcyclazacycloheptan-2-ones.

Depending on dosage form, the pharmaceutical compositions of the present invention may be administered in different ways, i.e., parenterally, topically, or the like. Preferred dosage forms are dosage forms that can be administered parenterally.

The amount of bioactive agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of alkyd polyester microdispersion incorporated into the parenteral, ointment, gel or cream will vary depending on the release profile desired and the amount of drug employed. The product may contain blends of polyesters to provide the desired release profile or consistency to a given formulation.

The alkyd polyester microdispersion, upon contact with body fluids including blood or the like, undergoes gradual degradation, mainly through hydrolysis, with concomitant release of the dispersed drug for a sustained or extended period, as compared to the release from an isotonic saline solution. This can result in prolonged delivery, e.g. over about 1 to about 2,000 hours, preferably about 2 to about 800 hours) of effective amounts, e.g. 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and alkyd polyester microdispersion may be tested in appropriate in vitro and in vivo models to achieve the desired drug release profiles. For example, a drug could be formulated with an alkyd polyester microdispersion and parenterally administered to an animal. The drug release profile could then be monitored by appropriate means, such as by taking blood samples at specific times and assaying the samples for drug concentration. Following this or similar procedures, those skilled in the art will be able to formulate a variety of formulations.

In a further embodiment of the present invention the injectable polymeric microdispersion can be used for a variety of soft tissue repair and augmentation procedures. For example, the microdispersions can be used in facial tissue repair or augmentation including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences (lips, brow, etc.). Additionally, these injectable microdispersions can be used to restore or improve sphincter function such as for treating stress urinary incontinence. Other uses of these injectable polymeric microdispersions may also include the treatment of vesicoureteral reflux (incomplete function of the inlet of the ureter in children) by subureteric injection and the application of these liquid polymers as general purpose fillers in the human body.

Surgical applications for injectable, biodegradable polymeric microdispersions include, but are not limited to, facial contouring (frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like); periurethral injection including injection into the submucosa of the urethra along the urethra, at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic affect. Surgical specialists who would use such a product include, but are not limited to, plastic and reconstructive surgeons, dermatologists, facial plastic surgeons, cosmetic surgeons, otolaryngologists, urologists, gynecologists, gastroenterologists, ophthalmologists and any other physician qualified to utilize such a product.

The polymeric microdispersions can be administered with a syringe and needle or a variety of devices. It is also envisioned that the microdispersions could be sold in the form of a kit comprising a device containing the microdispersions. The device having an outlet for said microdispersions, an ejector for expelling the microdispersions and a hollow tubular member fitted to the outlet for administering the microdispersions into an animal.

Additionally, the microdispersions, when sterilized, are useful as adhesion prevention barriers.

In another embodiment, the polymeric microdispersion is used to coat a surface of a surgical article to enhance the lubricity of the coated surface. The polymer may be applied as a coating using conventional techniques It is contemplated that numerous surgical articles, including but not limited to sutures, needles, orthopedic pins, clamps, screws, plates, clips, e.g. for vena cava, staples, hooks, buttons, snaps, bone substitutes, e.g. as mandible prosthesis, intrauterine devices, e.g. as spermicidal devices, draining or testing tubes or capillaries, surgical instruments, vascular implants or supports, e.g. stents or grafts, or combinations thereof, vertebral discs, extracorporeal tubing for kidney and heart-lung machines, artificial skin, and supports for cells in tissue engineering applications, can be coated with the polymeric microdispersions of this invention to improve the surface properties of the article.

In yet another embodiment, the medical device comprises a bone replacement material comprising the polymeric microdispersion. The bone replacement materials may further comprise microdispersion mixed with a bioactive agent in a therapeutically effective amount, such a growth factor, to facilitate growth of bone tissue. Examples of bioactive agents suitable for use with the present invention include cell attachment mediators, such as peptide-containing variations of the "RGD" integrin binding sequence known to affect cellular attachment, biologically active ligands, and substances that enhance or exclude particular varieties of cellular or tissue ingrowth. Examples of such substances include integrin binding sequence, ligands, bone morphogenic proteins, epidermal growth factor, IGF-I, IGF-II, TGF-β I-III, growth differentiation factor, parathyroid hormone, vascular endothelial growth factor, hyaluronic acid, glycoprotein, lipoprotein, bFGF, TGF superfamily factors, BMP-2, BMP-4, BMP-6, BMP-12, sonic hedgehog, GDF5, GDF6, GDF8, PDGF, small molecules that affect the upregulation of specific growth factors, tenascin-C, fibronectin, thromboelastin, thrombin-derived peptides, heparin-binding domains, and the like. Furthermore, the bone replacement material may comprise microdispersion mixed with a biologically derived substance selected from the group consisting of demineralized bone matrix (DBM), platelet rich plasma, bone marrow aspirate and bone fragments, all of which may be from autogenic, allogenic, or xenogenic sources.

Alternatively, the bone replacement material may comprise polymeric microdispersion mixed with an inorganic filler. The inorganic filler may be selected from alpha-tricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate. Preferably, the inorganic filler is hydroxyapatite.

The bone replacement materials may still further comprise polymeric microdispersion mixed with a bioactive agent in a therapeutically effective amount and an inorganic filler.

In still yet another embodiment, the bone replacement material may comprise polymeric microdispersion mixed with appropriate cell types prior to implantation. Cells which can be seeded or cultured in the polymeric microdispersions of the current invention include, but are not limited to, bone marrow cells, mesenchymal cells, stromal cells, stem cells, embryonic stem cells, osteoblasts, precursor cells derived from adipose tissue, bone marrow derived progenitor cells, peripheral blood progenitor cells, stem cells isolated from adult tissue, and genetically transformed cells, or combinations of the above.

The bone replacement polymeric microdispersions of the present invention may be used in applications such as the filling of trauma defects. Alternatively, they may be coated on orthopaedic devices to facilitate bone regeneration. Such devices include, but are not limited to plates, nails, screws, rods, and suture anchors.

Furthermore, the bone replacement polymeric microdispersions may be injected into, or coated on, naturally or synthetically derived tissue engineering scaffolds and spinal cages. Naturally derived tissue engineering scaffolds include those formed from small intestinal submucosa, collagen, hyaluronic acid, chitosan, and alginates. These scaffolds may be in the form of porous materials such as foams or sponges, or in fibrous form, such as weaves, braids, or nonwovens.

The relative amounts of polymeric microdispersion, bioactive agent, cells, and inorganic filler may be determined readily by one skilled in the art by routine experimentation after having the benefit of this disclosure.

The examples set forth below are for illustration purposes only, and are not intended to limit the scope of the claimed invention in any way. Numerous additional embodiments within the scope and spirit of the invention will become readily apparent to those skilled in the art.

In the examples below, the synthesized polymers were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of Poly(glyceryl monolinoleate-succinate)

29.97 gm (84.6 mmoles) of glyceryl monolinoleate were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 8.47 gm (84.6 mmoles) succinic anhydride were added and the temperature was raised to 200° C. Heat tape was wrapped around the outside of the top of the flask and adapter to keep the succinic anhydride from subliming. The reaction was continued for 3 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 ml EtOAc) and added to a separatory funnel. The solution was washed three times with 20 ml of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated to give a viscous yellow liquid. The polymer was dried in the vacuum oven, where the oven was set around 40° C., for 48 to 72 hours.

GPC measurements determined a number average molecular weight of 2,264, and a weight average molecular weight of 3,955 daltons.

EXAMPLE 2

Synthesis of Poly(glyceryl monolinoleate-succinate) High Molecular Weight

The same procedure as Example 1 was used, except the reaction was maintained at 200° C. for 24 hours.

GPC measurements determined a number average molecular weight of 6,624, and a weight average molecular weight of 83,214 daltons.

EXAMPLE 3

Synthesis of Poly(glyceryl monooleate-succinate)

30.0 gm (84.1 mmoles) glyceryl monooleate were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 8.42 gm (84.1 mmoles) succinic anhydride was added and the temperature was raised to 200° C. Heat tape was wrapped around the outside of the top of the flask and adapter to keep the succinic anhydride from subliming. The reaction was continued for 3 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 ml EtOAc) and added to a separatory funnel. The solution was washed three times with 20 ml of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated to give a viscous yellow liquid. The polymer was dried in the vacuum oven, where the oven was set around 40° C., for 48 to 72 hours.

GPC measurements determined a number average molecular weight of 2,145, and a weight average molecular weight of 3,659 daltons.

EXAMPLE 4

Synthesis of Poly(glyceryl monooleate-succinate)

The same procedure as Example 3 was used, except the reaction was maintained at 200° C. for 24 hours.

GPC measurements determined a number average molecular weight of 3,246, and a weight average molecular weight of 29,303 daltons.

EXAMPLE 5

Synthesis of 25:75 Poly(monostearoyl glycerol-co-glyceryl monolinoleate-succinate)

37.49 gm (105.8 mmoles) of glyceryl monolinoleate and 12.64 gm (35.3 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 14.1 gm (141.0 mmoles) succinic anhydride were added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer was a very viscous, light amber liquid.

For purification, the polymer was dissolved in Ethyl acetate (5.0 gm polymer in 20 ml EtOAc) and added to a separatory funnel. The solution was washed three times with 20 ml of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated down to give a viscous yellow liquid. The polymer was dried in the vacuum oven, where the oven was set around 40° C., for 48 to 72 hours.

DSC measurements found a melting point of about 20.0° C. GPC measurements determined a number average molecular weight of 2,115, and a weight average molecular weight of 3,326 daltons.

EXAMPLE 6

Synthesis of 75:25 Poly(monostearoyl glycerol-co-glyceryl monolinoleate-succinate)

12.5 gm (35.3 mmoles) of glyceryl monolinoleate and 37.92 gm (105.8 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 14.1 gm (141.0 mmoles) succinic anhydride was added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer crystallized to an amber, soft solid.

DSC measurements found a melting point of 46.43° C., and a specific heat of 45.36 J/g. GPC measurements determined a number average molecular weight of 2,210, and a weight average molecular weight of 3,722 daltons.

EXAMPLE 7

Synthesis of 25:75 Poly(monostearoyl glycerol-co-glyceryl monooleate-succinate)

44.12 gm (123.8 mmoles) of glyceryl monooleate and 14.79 gm (41.3 mmoles) monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 16.51 gm (165.0 mmoles) succinic anhydride was added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 ml EtOAc) and added to a separatory funnel. The solution was washed three times with 20 ml of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate for approximately one hour. The solution was gravity filtered and rotovapped down to give a viscous yellow liquid. The polymer was dried in the vacuum oven, where the oven was set around 40° C., for 48 to 72 hours. An $^1$H NMR was taken to make sure all of the solvent was removed.

DSC measurements found a melting point of 18.18° C., and a specific heat of 18.29 J/g. GPC measurements determined a number average molecular weight of 1,993, and a weight average molecular weight of 7,122 daltons.

EXAMPLE 8

Synthesis of 75:25 Poly(monostearoyl glycerol-co-glyceryl monooleate-succinate)

14.71 gm (41.3 mmoles) of glyceryl monooleate and 44.38 gm (123.8 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 16.51 g (165.0 mmol) succinic anhydride was added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer crystallized to an off white solid.

For purification, the polymer was dissolved in Ethyl acetate (5.0 gm polymer in 20 ml EtOAc) and added to a separatory funnel. The solution was washed three times with 20 ml of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate for approximately one hour. The solution was gravity filtered and rotovapped down to give a viscous yellow liquid. The polymer was dried in the vacuum oven, where the oven was set around 40° C., for 48 to 72 hours. An $^1$H NMR was taken to make sure all of the solvent was removed.

DSC measurements found a melting point of 44.78° C., and a specific heat of 66.94 J/g. GPC measurements determined a number average molecular weight of 1,966, and a weight average molecular weight of 3,200 daltons.

EXAMPLE 9

Synthesis of Poly(monostearoyl glycerol-co-succinate)

8.0 g (22.3 mmoles) of monostearoyl glycerol was added to a dry 50 ml, single neck, round bottom flask. A stir bar was added and a nitrogen inlet adapter was attached. The reaction flask was placed in a room temperature oil bath and a nitrogen gas blanket was started. The flask was heated to 140° C., and 4.46 gm (44.6 mmoles) of succinic anhydride was added. The temperature was raised to 200° C. and maintained for 3 hours. After 3 hours the flask was removed from the oil bath to cool to room temperature. Once the solution crystallized, it was deglassed and cleaned of any glass fragments. The polymer was an amber colored solid.

DSC measurements found a melt temperature of 46.84° C., and a specific heat of 63.57 J/g. GPC measurement determined a number average molecular weight of 2,688, and a weight average molecular weight of 5,848. The $^1$H NMR showed the following peaks: δ 0.86 triplet (3H), 1.26 multiplet (28H), 1.61 multiplet (2H), 2.30 multiplet (2H), 2.65 multiplet (4H), 4.16 multiplet (2H), 4.34 multiplet (2H), and 5.28 multiplet (2H).

EXAMPLE 10

Synthesis of Poly(monostearoyl glycerol-co-succinate)

The same procedure as Example 9 was used, except the reaction was maintained at 200° C. for 22.5 hours.

DSC measurements found a melt temperature of 48.41° C., and a specific heat of 73.98 J/g. GPC measurement determined a number average molecular weight of 2,546, and a weight average molecular weight of 43,002. The $^1$H NMR showed the same peaks as shown in Example 9.

EXAMPLE 11

Preparation of a poly(monostearoyl glycerol co succinate)/poly(glyceryl monooleate succinate) microdispersion This example illustrates the preparation of a microdispersion by melt blending and is suitable for use as an injectable medium for drug delivery. 7 gm of liquid poly(glyceryl monooleate succinate), as prepared in Example 3, and 3 gm of solid poly(monostearoyl glycerol co succinate), as prepared in Example 9, were added to a clean, scintillation vial. The vial was capped and immersed into an oil bath set at 55° C. and left for approximately 10 minutes. This melted the solid poly(monostearoyl glycerol co succinate) polymer. The vial was removed from the oil bath, the cap was removed and the melted polymer mixture was stirred until it cooled to room temperature. The resulting microdispersion had a paste-like consistency.

EXAMPLE 12

Sustained Release of Rapamycin from Microdispersion in vitro 1 gm of the microdispersion described in Example 11 was placed in scintillation vial. The vial was capped and immersed into an oil bath set at 50° C. and left for approximately 10 minutes. 30 mg of rapamycin (Wyeth-Ayerst Madison, N.J.), was added to the microdispersion and mixed immediately with a spatula.

20 mg of the above microdispersion containing rapamycin was applied to the inner wall of a pre-weighed 15 ml conical tube. 5 ml of phosphate buffered saline was added to the tube. The sample was incubated at 37° C. on a shaker plate (90 rpm) for two weeks. At daily time points, 500 □L of the supernatant was loaded into a 96 well plate and the optical density at 287 nm was measured by a spectrophotometer. Rapamycin in methanol standards (100, 75, 50, 25, 1 □g/ml) were also loaded into 96 well plate to obtain a standard curve. Sample aliquots were returned to conical tubes after analysis.

The total amount of rapamycin released in 15 days was 0.34 mg (58%).

We claim:

1. A composition, comprising: a microdispersion, said microdispersion comprising a synthetic, bioabsorbable, biocompatible liquid polymer having a melting point less than about 40° C., as determined by differential scanning calorimetry; and a synthetic, bioabsorbable, biocompatible polymeric wax having a melting point less than about 70° C., as determined by differential scanning calorimetry, wherein said liquid polymer and said polymeric wax comprise the reaction product of a polybasic acid or derivative thereof and a monoglyceride, said liquid polymer comprises an aliphatic polyester backbone with first pendant fatty acid ester groups and said polymeric wax comprises an aliphatic polyester backbone with second pendant fatty acid ester groups, wherein said first and second fatty acid groups are not the same.

2. The composition of claim 1 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

3. The composition of claim 1 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

4. The composition of claim 3 wherein said polybasic acid derivative is succinic anhydride.

5. The composition of claim 3 wherein said polybasic acid is succinic acid.

6. The composition of claim 1 wherein said polymeric wax comprises the reaction product of said monoglyceride, and at least two of said polybasic acids or derivatives thereof selected from the group consisting of succinic acid, succinic anhydride, malic acid, tartaric acid, citric acid, diglycolic acid and diglycolic anhydride.

7. The composition of claim 1 wherein said polymeric wax comprises the reaction product of said polybasic acid or derivative thereof, and at least two of said monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

8. The composition of claim 1 wherein said polymeric wax comprises the reaction product of said polybasic acid or derivative thereof, said monoglyceride selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol, and at least one polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

9. The composition of claim 1 wherein at least one of said liquid polymer and said polymeric wax comprises an end capping-moeity selected from the group consisting of alkyls, alkenyls, alkynyls, acrylates, methacrylates, amines, isocyanates and isothiocyanates.

10. The composition of claim 1, further comprising an effective amount of a bioactive agent.

11. The composition of claim 10 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid and derivatives thereof.

12. The composition of claim 10 wherein said monoglyceride is selected from the group consisting of monostearoyl glycerol, monopalmitoyl glycerol, monomyrisitoyl glycerol, monocaproyl glycerol, monodecanoyl, monolauroyl glycerol, monolinoleoyl glycerol and monooleoyl glycerol.

13. The composition of claim 12 wherein said polybasic acid derivative is succinic anhydride.

14. The composition of claim 12 wherein said polybasic acid is succinic acid.

15. The composition of claim 10 wherein said bioactive agent is selected from the group consisting of antiinfectives, analgesics, anorexics, antihelmintics, antiarthritics, antiasthmatics, anticonvulsants, antidepressants, antidiuretics, antidiarrheals, antihistamines, antiinflammatory agents, antimigraine preparations, antinauseants, antineoplastics, antiparkinsonism drugs, antipruritics, antipsychotics, antipyretics, antispasmodics, anticholinergics, sympathomimetics, xanthine derivatives, calcium channel blockers, betablockers, antiarrhythmics, antihypertensives, diuretics, vasodilators, central nervous system stimulants, decongestants, hormones, steroids, hypnotics, immunosuppressives, muscle relaxants, parasympatholytics, psychostimulants, sedatives, tranquilizers, naturally derived or genetically engineered proteins, polysaccharides, glycoproteins, or lipoproteins, oligonucleotides, antibodies, antigens, cholinergics, chemotherapeutics, hemostatics, clot dissolving agents, radioactive agents and cystostatics.

16. The composition of claim 10 wherein said bioactive agent is risperidone.

17. The composition of claim 10 wherein said bioactive agent is erythropoietin.

18. The composition of claim 10 wherein said bioactive agent is rapamycin.

19. A medical device comprising a coating of said microdispersion, said microdispersion comprising a synthetic, bioabsorbable, biocompatible liquid polymer having a melting point less than about 40° C., as determined by differential scanning calorimetry; and a synthetic, bioabsorbable, biocompatible polymeric wax having a melting point less than about 70° C., as determined by differential scanning calorimetry, wherein said liquid polymer and said polymeric wax comprise the reaction product of a polybasic acid or derivative thereof, and a monoglyceride, wherein said monoglyceride comprises reactive hydroxyl and fatty acid groups, and wherein said liquid polymer comprises an aliphatic polyester backbone with first pendant fatty acid ester groups and said polymeric wax comprises an aliphatic polyester backbone with second pendant fatty acid ester groups, wherein said first and second fatty acid groups are not the same.

20. The composition of claim 1 comprising a soft tissue repair material comprising said microdispersion.

21. The composition of claim 1 comprising a soft tissue augmentation material comprising said microdispersion.

22. The medical device of claim 19 comprising a surgical article selected from the group consisting of sutures, stents, needles, vascular grafts, stent-graft combinations, meshes, tissue engineering scaffolds, pins, clips, staples, films, sheets, foams, anchors, screws and plates.

23. The composition of claim 1 comprising a bone replacement material comprising said microdispersion.

24. The composition of claim 23 further comprising a therapeutically effective amount of a bioactive agent.

25. The composition of claim 24 wherein said bioactive agent is a growth factor.

26. The composition of claim 25 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-β-I-III, growth differentiation factor, parathyroid hormone, vascular endothelial growth factor, hyaluronic acid, glycoprotein, lipoprotein, bFGF, TGF superfamily factors, BMP-2, BMP-4, BMP-6, BMP-12, sonic hedgehog, GDF5, GDF6, GDF8, PDGF, tenascin-C, fibronectin, thromboelastin, and thrombin-derived peptides.

27. The composition of claim 23 further comprising a biologically derived substance selected from the group consisting of demineralized bone, platelet rich plasma, bone marrow aspirate and bone fragments.

28. The composition of claim 23 further comprising an inorganic filler.

29. The composition of claim 28 wherein said inorganic filler is selected from the group consisting of alpha-tricalcium phosphate, beta-tricalcium phosphate, calcium carbonate, barium carbonate, calcium sulfate, barium sulfate and hydroxyapatite.

30. The composition of claim 28 wherein said inorganic filler is hydroxyapatite.

* * * * *